United States Patent [19]

Lawson

[11] 4,321,386

[45] Mar. 23, 1982

[54] QUATERNARY PIPERIDINIUM HALIDES

[75] Inventor: John E. Lawson, Evansville, Ind.

[73] Assignee: Mead Johnson & Company, Evansville, Ind.

[21] Appl. No.: 229,244

[22] Filed: Jan. 28, 1981

[51] Int. Cl.[3] .......................................... C07D 211/34
[52] U.S. Cl. .................................................. 546/234
[58] Field of Search ........................................ 546/234

[56] References Cited

U.S. PATENT DOCUMENTS 3,931,195  1/1976  Dykstra et al. ................... 546/234

OTHER PUBLICATIONS

Dykstra, S. J. et al., Jour. Med. Chem., vol. 16 (1973) pp. 1015–1020.

Byrne, J. E., et al., Jour. Pharmacology and Experimental Therapeutics, vol. 200 (1977) pp. 147–154.

*Primary Examiner*—Norma S. Milestone
*Attorney, Agent, or Firm*—Robert H. Uloth; Robert E. Carnahan

[57] ABSTRACT

2-[2-[2-[(4-Methoxybenzoyl)amino]phenyl]ethyl]-1-methyl-1-alkylpiperidinium halides and 2-[2-[2-[(4-methoxybenzoyl)amino]phenyl]ethyl]-1-methyl-1-benzylpiperidinium halides are antiarrhythmic agents having reduced toxicity relative to the corresponding piperidine compound.

3 Claims, No Drawings

QUATERNARY PIPERIDINIUM HALIDES

FIELD OF THE INVENTION

2-[2-[2-[(4-Methoxybenzoyl)amino]phenyl]ethyl]-1-methyl-1-alkylpiperidinium halides and 2-[2-[2-[(4-methoxybenzoyl)amino]phenyl]ethyl]-1-methyl-1-benzylpiperidium halides are heterocyclic carbon compounds of the quaternary piperidinium series having an additional ring and having nitrogen attached indirectly to the piperidine ring by non-ionic bonding (Class 546, Subclass 229).

DESCRIPTION OF THE PRIOR ART

The corresponding piperidine compound, encainide, is an antiarrhythmic compound which is also referred to in the literature as MJ 9067 (USAN And The USP Dictionary of Drug Names 1980, page 122, United States Pharmacopeial Convention, Inc., 12601 Twinbrook Parkway, Rockville, MD 20852, Library of Congress Catalog Card No. 72-88571).

Encainide has structural formula I

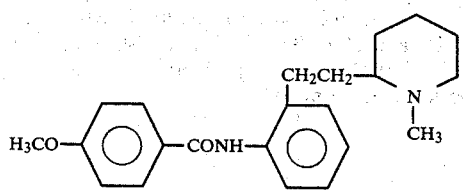

The following publications describe the chemical synthesis of encainide and its antiarrhythmic properties in animals.

Dykstra, S. J., et al., J. Med. Chem., 16, 1015–1020 (1973).

Stanley J. Dykstra and Joseph L. Minielli, U.S. Pat. No. 3,931,195 patented Jan. 6, 1976.

Byrne, J. E., et al., J. Pharmacology and Experimental Therapeutics, 200, 147–154 (1977).

The N-oxide derivatives of encainide as an antiarrhythmic agent is the subject of a co-pending application Serial No. 160,900 filed June 19, 1980.

SUMMARY OF THE INVENTION

The present invention is concerned with quaternary piperidinium halides which have structural formula II, where R is lower alkyl of 1–4 carbon atoms inclusive or benzyl and X is halide such as chlorine, bromine, iodine.

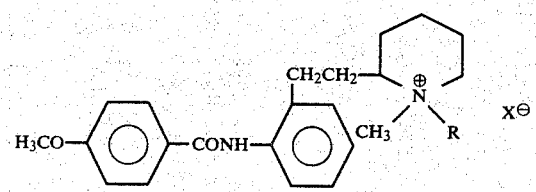

These substances are improved antiarrhythmic agents. In the chloroform induced arrhythmia test in the mouse the subject compounds are several times more active than quinidine and only a little less active than encainide. In toxicity testing in mice, these quaternary compounds are several times less toxic than encainide. They are thus antiarrhythmic agents of substantial potency and they offer the advantage over encainide of reduced toxicity. They may be administered in the same fashion as encainide. Higher doses, if necessary, in relation to their comparative toxicities may be employed for the treatment of cardiac arrhythmias.

DESCRIPTION OF SPECIFIC EMBODIMENTS

The compounds which constitute this invention, their methods of preparation, and their biologic actions will appear more fully from a consideration of the following examples and appended claims which are given for the purpose of illustration only and are not to be construed as limiting the invention in sphere or scope.

The process used for preparation of compounds of formula II in the present invention involves heating approximately stoichiometric quantities of encainide (I) and R-X, (where R is lower alkyl of 1–4 carbon atoms inclusive or benzyl; and X is halide such as chlorine, bromine, iodine) in a suitable organic solvent at reflux for a period of time ranging from 6 to 24 hours. Acetone is a preferred solvent for carrying out the process although other solvents employed in forming quaternary ammonium salts such as acetonitrile, benzene, chloroform, methanol, dichloroethane, and others are generally operable. The solvent is evaporated and the reaction residue distributed between $H_2O$ and benzene. The aqueous layer is separated, washed twice with benzene, and evaporated in vacuo to obtain a solid product of formula II.

A comparison of some biologic properties of encainide (I) and two representative examples of formula II (IIa: $R=CH_3$, $X=I$; IIb: $R=CH_2Ph$, $X=Br$) is given in the following table.

| Property | I | IIa | IIb |
|---|---|---|---|
| Toxicity | | | |
| $ALD_{50}^{(1)}$ | 50–100 mg/kg | >2000 mg/kg | >1000 mg/kg |
| $ATD_{50}^{(1)}$ | 5–10 mg/kg | 250 mg/kg | 125–250 mg/kg |
| Antiarrhythmic Activity | | | |
| Mouse$^{(2)}ED_{50}$ | 7–15 mg/kg | 30.5 mg/kg | 19 mg/kg |

$^{(1)}$Various oral doses of from 5 mg/kg to 2000 mg/kg are given to 2 mice each; $ALD_{50}$ is the approximate lethal dose for half the animals; $ATD_{50}$ is the approximate lowest dose where signs of physiologic or neurologic deficit appear.
$^{(2)}$Ventricular arrhythmia produced in mice by chloroform inhalation, 10 animals per dose (Lawson, J. W., J. Pharmacol. Exp. Therap., 160, 22 (1968)).

With reference to the spectral data given below in the examples:

The nuclear magnetic resonance (NMR) values refer to chemical shifts ($\delta$) expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), or multiplet (m). The format is NMR (solvent): $\delta$ (relative area, multiplicity). The infrared (IR) was measured on a dispersion of the solid material in crystalline potassium bromide. The wave of significant absorption maxima are listed.

EXAMPLE 1

2-[2-[2-[(4-Methoxybenzoyl)amino]phenyl]ethyl]-1,1-dimethylpiperidinium Iodide (IIa)

A solution of 7.04 g (0.020 mol) of encainide (I) and 5.68 g. (0.040 mol) of methyl iodide in 100 ml. of acetone was heated at the reflux temperature for 24 hours.

The solvent was evaporated and the residue was distributed between H₂O and benzene. The aqueous layer was separated, washed twice with benzene, and evaporated in vacuo to obtain a solid, m.p. 75°–80° C.

Anal. Calcd. for $C_{23}H_{31}N_2O_2I$: C, 55.88; H, 6.32; N, 5.67. Found: C, 55.74; H, 6.48; N, 5.58.

NMR: DMSO-$d_6$: 1.65 (8,m); 2.87 (3,s); 2.90 (5,m); 3.01 (3,s); 3.84 (3,s); 7.22 (6,m); 7.98 (2,m); 9.75 (1,bs).

IR: 768, 1175, 1255, 1310, 1490, 1500, 1608, 1650, 2940, 3240 cm$^{-1}$.

EXAMPLE 2

2-[2--[2-[(4-Methoxybenzoyl)amino]phenyl]ethyl]-1-methyl-1-(phenylmethyl)piperidinium Bromide Hydrate (IIb)

A solution of 3.52 g. (0.010 mol) of encainide (I) and 1.71 g. (0.010 mol) of benzyl bromide was heated at the reflux temperature for 24 hours. The reaction mixture then was worked up as described in Example 1. There was obtained 2.80 g., m.p. 135°–140° C.

Anal. Calcd. for $C_{29}H_{35}N_2O_2Br \cdot 0.25\ H_2O$: C, 65.97; H, 6.78; N, 5.31; H₂O, 0.85. Found: C, 65.68; H, 6.79; N, 5.23; H₂O, 1.16.

NMR: DMSO-$d_6$: 1.70 (8,m); 2.86 (3,s); 3.00 (5,m); 3.79, 3.82 [3,2s (2:1)]*; 4.50 (2,m); 7.00 (2,m); 7.40 (9,m); 9.01 (2,m)*; 9.89 (1,bs).

*These patterns indicate a 2:1 isomer mixture in DMSO-$d_6$ solution of stereoisomers due to dissymetry imposed in this molecule by the quaternary nitrogen configuration.

IR: 770, 1170, 1255, 1312, 1500, 1610, 1655, 2950, 3220 cm$^{-1}$.

What is claimed is:

1. A compound having Formula II

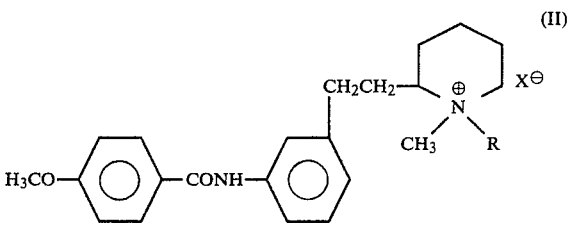

wherein R is lower alkyl or benzyl and X is halide.

2. The compound (IIa) of claim 1 where R is —CH₃ and X is I which is 2-[2-[2-[(4-methoxybenzoyl)amino]phenyl]ethyl]-1,1-dimethylpiperidinium iodide.

3. The compound (IIb) of claim 1 where R is —CH₂C₆H₅ and X is Br which is 2-[2-[2-[(4-methoxybenzoyl)amino]phenyl]ethyl]-1-methyl-1-(phenylmethyl)piperidinium bromide.

* * * * *